United States Patent [19]
Brady et al.

[11] Patent Number: 5,457,221
[45] Date of Patent: Oct. 10, 1995

[54] PROCESS FOR THE MANUFACTURE OF POLY (HYDROCARBYLENE ARYL PHOSPHATE) COMPOSITIONS

[75] Inventors: Bill L. Brady, Gallipolis, Ohio; Danielle A. Bright, New City, N.Y.; Francis M. Schafer, Point Pleasant, W. Va.

[73] Assignee: Akzo Nobel N.V., Arnhem, Netherlands

[21] Appl. No.: 152,546

[22] Filed: Nov. 15, 1993

Related U.S. Application Data

[63] Continuation-in-part of Ser. No. 25,708, Mar. 3, 1993, abandoned.

[51] Int. Cl.$^6$ ..................................................... C07F 9/12
[52] U.S. Cl. ............................................................ 558/99
[58] Field of Search .................................................. 558/99

[56] References Cited

U.S. PATENT DOCUMENTS

| | | | |
|---|---|---|---|
| 3,254,973 | 6/1966 | Giammaria et al. | 44/69 |
| 3,965,220 | 6/1976 | Schumacher | 260/975 |
| 4,035,449 | 7/1977 | Zakaryan | 260/972 |
| 4,133,846 | 1/1979 | Albright | 260/928 |
| 5,097,056 | 3/1992 | Segall et al. | 558/110 |
| 5,122,556 | 6/1992 | Kambour | 524/141 |

FOREIGN PATENT DOCUMENTS

| | | | |
|---|---|---|---|
| 2034403 | 10/1991 | Canada | C08L 69/0 |
| 509506 | 10/1992 | European Pat. Off. | C07F 9/12 |
| 0521628 | 1/1993 | European Pat. Off. | C07F 9/12 |
| 227632 | 9/1988 | Japan | C08G 79/04 |

OTHER PUBLICATIONS

Chemical Abstracts, vol. 81, 14599m (1974).
Chemical Abstracts, vol. 84, 89741x (1976).
Derwent Abstract of JP 57/174331 (Oct. 1982).
Derwent Abstract of JP 89/31544 (1982).
Chemical Abstracts of U.S. Pat. No. 2,520,090 (1952) #7589i.

*Primary Examiner*—Johann Richter
*Assistant Examiner*—Michael G. Ambrose
*Attorney, Agent, or Firm*—Richard P. Fennelly; Louis A. Morris

[57] ABSTRACT

Arylene poly(diarylphosphate) compositions can be formed by a process which comprises:

(a) forming a reaction mixture comprising diaryl halophosphate and, as by-products, a mixture of monoaryl dihalophosphate and triarylphosphate, by reaction of phosphorus oxyhalide and a phenol in a first reactor;

(b) if a preponderance of lower oligomers is desired, optionally transferring the reaction mixture from (a) to a subsequent reactor where at least a portion of the monoaryl dihalophosphate is recycled to the first reactor for reaction with the phenol contained therein to form additional diaryl halophosphate in the first reactor and the reaction mixture in (b) becomes enriched with diaryl halophosphate to ultimately favor the ultimate formation of a product of lower molecular weight distribution; and (c) reacting the product from (a) or (b), as selected, with an aromatic diol to form the arylene poly(diarylphosphate) product.

8 Claims, 1 Drawing Sheet

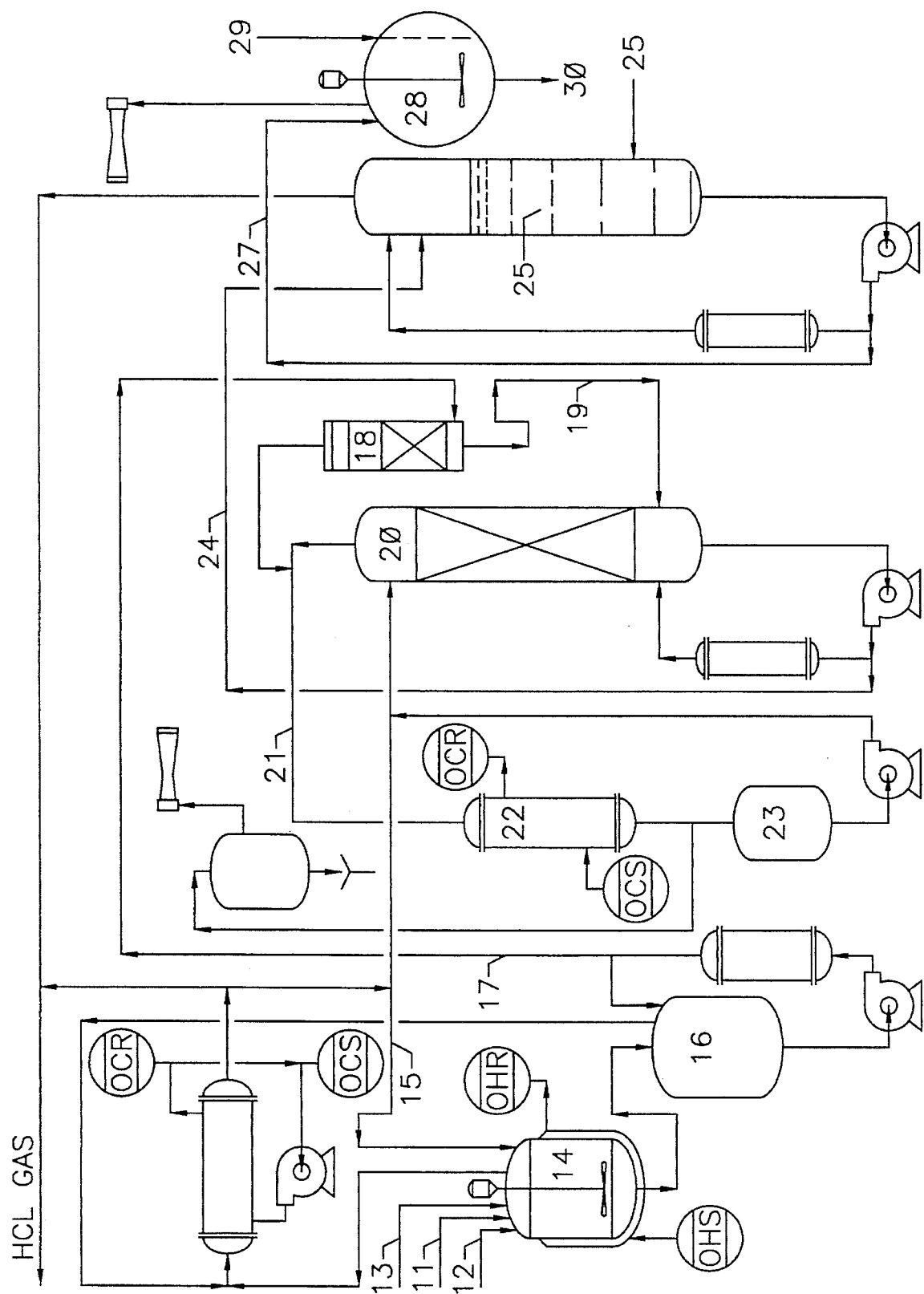

PROCESS FOR THE MANUFACTURE OF POLY (HYDROCARBYLENE ARYL PHOSPHATE) COMPOSITIONS

This is a continuation in part of U.S. Ser. No. 08/025,708, filed Mar. 3, 1993, abandoned.

BACKGROUND OF THE INVENTION

Poly(hydrocarbylene aryl phosphate) compositions of the formula

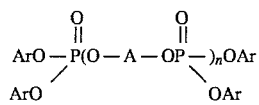

where Ar is either unsubstituted or substituted aryl, A is a hydrocarbylene bridging group comprising, for example, alkylene, arylene, two arylene groups joined by a bridging group (e.g., —C(CH$_3$), —SO$_2$ or —CO), or biarylene, and n is equal or greater than 1 are a known class of flame retardant. Such compositions typically are a blend of the "bis"phosphate, where n=1, and higher oligomers, where n is an integer greater than 1. The term "poly" is used herein to include both the "bis"phosphate composition as well as the higher oligomers.

One technique for formation of such compositions involves the initial reaction of a phosphorus oxyhalide (e.g., phosphorus oxytrichloride) with an aromatic diol (e.g., bisphenol A resorcinol or hydroquinone) followed by the reaction of the resulting reaction product with, for example, an aromatic hydroxy compound (e.g., phenol). Examples of this route are described in U.S. Pat. No. 2,520,090 and Japanese Patent Publication Nos. 89/31,544, 57/174,331 and 88/227,632. These routes are plagued by the large excess of phosphorus oxytrichloride needed to achieve a high content of dimer as product, for example, and the relatively long time needed to strip excess phosphorus oxytrichloride from the reaction vessel. Also, the stripping of phosphorus oxytrichloride from the reaction mixture prior to addition of phenol for long periods of time at relatively high temperatures, to lessen the ultimate amount of triphenyl phosphate, for example, that is present in the final product, can result in an undesired change in the desired composition which results.

While it is known to form compounds of the formula (ArO)$_2$P(O)Cl (see U.S. Pat. No. 3,965,220), only a few disclosures are known to exist in which such polyphosphate compounds are formed in which the initial reaction is between monohydroxy compound and phosphorus oxychloride with the second reaction step using diol as the reagent. In U.S. Pat. No. 4,133,846 it is taught in Example 4 that bis(2-chloroethyl) chlorophosphate and pentaerythritol were to be reacted to form the desired product. Presumably, the bis(2-chloroethyl) chlorophosphate could be formed by reaction of phosphorus oxytrichloride and appropriate monohydroxy compound (i.e., 2-chloroethanol). U.S. Pat. No. 3,254,973, at Col. 5, line 66 and following, illustrates preparation of 4,4'-isopropylidene diphenol bis(di-o-tolylphosphate) by first reacting phosphorus oxychloride with o-cresol to form a reaction mixture in which di-o-tolyl phosphorochloridate cuts are removed by distillation. The di-o-tolyl phosphorochloridate from the first reaction step was then reacted with the diol (i.e., bisphenol A) to make the desired bisphosphate.

SUMMARY OF THE INVENTION

The present invention, in one embodiment where a higher amount of the higher oligomers of the above-described compositions is desired, comprises:

(a) forming a reaction mixture comprising diaryl halophosphate and, as by-products, a mixture of monoaryl dihalophosphate and triarylphosphate, by reaction of phosphorus oxyhalide and a phenol (either phenol itself or a substituted phenol) in a reactor; and (b) reacting the product from (a) with an aromatic diol to form the arylene poly(diarylphosphate).

The present invention, in the embodiment where a greater preponderance of lower oligomers is desired as compared to the previously described embodiment, is a process for the formation of a poly(hydrocarbylene aryl phosphate) composition which comprises:

(a) forming a reaction mixture comprising diaryl halophosphate and, as by-products, a mixture of monoaryl dihalophosphate and triarylphosphate, by reaction of phosphorus oxyhalide and a phenol in a first reactor;

(b) transferring the reaction mixture from (a) to a subsequent reactor where at least a portion of the monoaryl dihalophosphate is recycled to the first reactor for reaction with the phenol contained therein to form additional diaryl halophosphate in the first reactor and the reaction mixture in (b) becomes enriched in diaryl halophosphate to favor the ultimate production of higher amounts of the bisphosphate compound and correspondingly lower amounts of the higher oligomeric product(s); and (c) reacting the product from (b) with an aromatic diol to form the arylene poly(diarylphosphate).

The present process gives the person of ordinary skill in the art the ability to produce compositions of desired compositional distribution of bisphosphate and higher oligomers depending on the particular ratio of DPCP to MPCP, for example, present when the reaction with the aromatic diol is conducted. This relationship between the ratio of the monohalophosphate/dihalophosphate ratio and the ultimate bis/oligomeric nature of the final product was not appreciated heretofore. If a higher amount of oligomer is desired, the ratio of DPCP/MPCP, for example, is lowered. If higher amounts of the lower oligomers is desired, it is raised.

DESCRIPTION OF THE DRAWING

The present invention is further understood by reference to the Drawing, which forms a portion of the instant Specification. This Drawing is a schematic of the reaction section for a plant production facility which utilizes the instant process for the manufacture of a particularly preferred arylene poly(diarylphosphate) compound.

DETAILED DESCRIPTION OF THE INVENTION

The Drawing sets forth a preferred reaction configuration for the manufacture of resorcinol bis(diphenylphosphate) in accordance with the present invention. This particular reaction configuration, however, is not to be construed as limiting the scope of the present invention since it is well within the skill of the person in the art to adapt to depicted reaction configuration to the manufacture of other arylene poly(diarylphosphate) compounds. The use of the word "compound" as used herein, in connection with the preferred embodiment to be described below, is intended to cover compositions comprising a major amount of the desired compound, containing the desired bisphosphate structure, and minor amounts of higher oligomers in which three or more phosphate moieties are present. However, it is to be recognized that the claimed process is quite flexible in regard to the amount of bisphosphate or higher oligomers which are present as will be described in greater detail below. As shown in Examples 1–6, below, the presence of higher ratios of the monochloro species (e.g., diphenyl chlorophosphate) as compared to the amount of dichlorophosphate (e.g., monophenyl dichlorophosphate) will favor the production of lower molecular weight species.

Phosphorus oxytrichloride ($POCl_3$) in line 11, phenol in line 12, and magnesium chloride catalyst in line 13, are appropriately fed to reactor 14. Catalyst loading to reactor 14 is preferably between about 150 and about 300 ppm, typically about 160 ppm based on the final product. Reactor 14 is maintained at a slight positive pressure and at about 105° to about 160° C., typically about 110° C. to yield diphenyl chlorophosphate (DPCP) by the reaction of phosphorus oxytrichloride and phenol. An excess of monophenyl dichlorophosphate (MPCP) is maintained in reactor 14 by recycle of MPCP via line 15 from later stages of the reaction, as will be described in greater detail below. The reaction material from reactor 14 is moved to tank 16 for further reaction completion. Tank 16 is maintained at a slight positive pressure and at about 185° C. to about 220° C., typically about 195° C. The abbreviations "OHS" and "OHR" to reactor 14 refer to "oil hot supply" and "oil hot return", respectively.

The reaction mixture from tank 16 is pumped via line 17 to reactor 18. The liquid from tower 18 flows via line 19 to stripping tower 20. Tower 20 is maintained at about 170° C. to about 205° C., typically about 180° C. and a vacuum of about 75 mm Hg or less to remove the excess MPCP. The MCPC vapor streams from tower 18 and tower 20 are combined in line 21, are condensed in exchanger 22, and are collected in vessel 23 for eventual recycle via line 15 to reactor 14. The abbreviations "OCS" and "OCR" to exchanger 22 refer to "oil cooling supply" and "oil cooling return", respectively.

The DPCP, after the stripping of excess MPCP therefrom, is pumped via line 24 to reactor 25 into which resorcinol, which has been flash distilled and treated to remove it from its color bodies, is pumped via line 26. Reactor 25 is maintained at a slight positive pressure and about 150° C. to about 170° C., typically about 160° C. A slight excess of resorcinol is fed into reactor 25. The crude product from reactor 25 is fed via line 27 to reactor 28 to which is added additional catalyst, for example, magnesium chloride, in line 29. Catalyst loading to reactor 28 can range from about 75 ppm to about 150 ppm, typically about 80 ppm, based on the finished product. Reactor 28 is maintained at from about 160° C. to about 190° C., typically about 175° C. and a vacuum of about 100 mm Hg or less. The conditions in reactor 28 insure a more complete conversion of the DPCP to the desired reaction product, resorcinol bis diphenylphosphate. The product from reactor 28 is then taken for further purification to remove the catalyst and trace impurities from the product.

By-product hydrogen chloride from reactor 14, vessel 16, and reactor 25 are combined and absorbed into demineralized water to make muriatic acid.

One advantage of the present process over the phosphorus oxytrichloride processes described before is the ability to produce compositions of desired compositional distribution of bisphosphate and higher oligomers depending on the particular ratio of DPCP to MPCP, for example, present when the reaction with the aromatic diol is conducted. This relationship between the ratio of the monohalophosphate/dihalophosphate ratio and the ultimate bis/oligomeric nature of the final product was not appreciated heretofore.

The present invention is further understood by the Examples which follow.

EXAMPLES 1–4

A 500 ml 4-necked flask equipped with mechanical stirrer, nitrogen inlet and outlet, thermometer, reflux condenser was charged with 180 g (0.67 mole) of diphenyl chlorophosphate (DPCP) and 20.0 g (0.095 mole) of monophenyl dichlorophosphate (MPCP), weight ratio of DPCP to MPCP 90:10, 47.3 g of resorcinol (0.43 mole), and 250 mg of magnesium chloride. The reaction mixture was heated to 150° C. At 130° C., the hydrogen chloride evolution was quite fast. The reaction was complete (as measured by the amount of hydrogen chloride evolved) after four hours.

The reaction mixture was washed at 60° C. with 2×200 ml of 2% caustic, followed by 3×200 ml of water. After removal of traces of water, under vacuum and at 80° C., there was left 195.2 g of a light yellow oil (90% yield).

Table 1 shows the oligomer distribution of the product as a function of the ratio of DPCP to MPCP that was used in this run and three others where the DPCP/MPCP ratio was varied.

TABLE 1

| DPCP/MPCP | TPP | TPPOH | $P_2$ | $P_3$ | $P_4$ | $P_5$ | $P_6$ | $P_7$ |
|---|---|---|---|---|---|---|---|---|
| 95:5 | 2.6 | 0.28 | 78.1 | 14.4 | 2.9 | 0.72 | — | — |
| 92:8 | 2.4 | ND | 70.7 | 18.8 | 5.3 | 1.4 | 0.4 | 0.11 |
| 90:10 | 2.7 | 0.23 | 66.1 | 20.4 | 6.7 | 2.2 | 0.66 | 0.17 |
| 85:15 | 2.2 | 0.36 | 55.4 | 23.5 | 10.4 | 4.3 | 1.7 | 0.63 |
| 50:50 | 1.4 | — | 18.1 | 15.0 | 12.0 | 9.9 | 8.1 | 7.2 |
| 15:85 | — | — | 4.9 | 4.8 | 5.1 | 5.3 | 5.0 | 4.8 |

TPP = triphenylphosphate
TPPOH = 3-hydroxyphenyl diphenylphosphate
$P_2$–$P_7$ = Indicates the number of phosphorus atoms in the respective by-products of the reaction. The preferred number is two for the intended diphosphate product.

In the experimental work given above, the oligomer ranges, as reflected by the number of phosphorus atoms, and the DPCP/MPCP ratios were related as follows:

| DPCP/MPCP Ratio | Number of Phosphorus Atoms |
|---|---|
| 95:5 | 1–5 |
| 92:8 | 1–7 |
| 90:10 | 1–8 |
| 85:15 | 1–9 |
| 50:50 | 1–14 |
| 15:85 | 1–22 |

The foregoing Examples are presented for illustrative purposes only and, for this reason, should not be construed in a limiting sense. The scope of protection that is sought is set forth in the claims which follow.

We claim:

1. A process for the formation of an poly(hydrocarbylene aryl phosphate) composition which comprises:
   (a) forming a reaction mixture comprising diaryl halophosphate and, as by-products, a mixture of monoaryl dihalophosphate and triarylphosphate, by reaction of phosphorus oxytrihalide and a phenol in a first reactor;

(b) transferring the reaction mixture from (a) to a subsequent reactor where at least some of the monoaryl dihalophosphate is recycled to the first reactor for reaction with the phenol contained therein to form additional diaryl halophosphate in the first reactor and the reaction mixture in (b) becomes enriched with diaryl halophosphate to thereby ultimately favor a higher production of lower molecular weight product; and (c) reacting the product from (b) with an aromatic diol to form the arylene poly(diarylphosphate) product.

2. A process as claimed in claim 1 wherein the phosphorus oxyhalide is phosphorus oxytrichloride.

3. A process as claimed in claim 1 wherein the phenol is phenol.

4. A process as claimed in claim 1 wherein the phosphorus oxyhalide is phosphorus oxytrichloride and the phenol is phenol.

5. A process as claimed in claim 1 wherein the aromatic diol is resorcinol.

6. A process as claimed in claim 2 wherein the aromatic diol is resorcinol.

7. A process as claimed in claim 3 wherein the aromatic diol is resorcinol.

8. A process as claimed in claim 4 wherein the aromatic diol is resorcinol.

* * * * *